United States Patent [19]
Engel et al.

[11] Patent Number: 5,834,520
[45] Date of Patent: Nov. 10, 1998

[54] CONTAINER FOR INJECTABLE MESNA SOLUTIONS

[75] Inventors: Jürgen Engel, Alzenau; Elisabeth Wolf-Heuss, Mosbach; Wolfgang Deger; Giancarlo Camuglia, both of Frankfurt; Dieter Sauerbier, Werther, all of Germany

[73] Assignee: ASTA-Medica Aktiengesellschaft, Dresden, Germany

[21] Appl. No.: 915,586

[22] Filed: Aug. 21, 1997

Related U.S. Application Data

[63] Continuation of Ser. No. 474,247, Jun. 7, 1995, abandoned, and a division of Ser. No. 132,180, Oct. 6, 1993, abandoned.

[30] Foreign Application Priority Data

Oct. 8, 1992 [DE] Germany ............................ 42 33 842.5

[51] Int. Cl.$^6$ ................................................ A61K 31/095
[52] U.S. Cl. ............................................................ 514/706
[58] Field of Search .............................................. 514/706

[56] References Cited

U.S. PATENT DOCUMENTS 4,720,379   1/1988   Heyl et al. ................................ 424/10

FOREIGN PATENT DOCUMENTS 3111770   5/1991   Germany .

OTHER PUBLICATIONS

Cerny et al., Bioavailability of subcutaneous Ifosfamide and feasibility of continuous outpatient application in cancer patients, Anals of Oncology, vol. I, pp. 365–368, 1990.

Kwon et al., "Activation Mechanisms of Mafosfamide and the Role of Thiols in Cyclophosphamide Metabolism", J.Med.Chem. 1987, vol. 30, pp. 395–399.

Leeuwenkamp, et al., Reaction Kinetics of Cisplatin and its Monoaquated Species with the Modulating Agents (Di)mesna and Thiosulphate, Eur.J.Cancer, vol. 27, No. 10, pp. 1243–1247, 1991.

Rote Liste 1992.

Primary Examiner—Theodore J. Criares
Attorney, Agent, or Firm—Cushman Darby&Cushman IP Group of Pillsbury Madison & Sutro LLP

[57] ABSTRACT

Injectable mesna solutions having a pH value higher than 7.5. The solutions have increased storage stability.

2 Claims, No Drawings

CONTAINER FOR INJECTABLE MESNA SOLUTIONS

This is a continuation of application Ser. No. 08/474,247, filed on Jun. 7, 1995, which was abandoned, which is a division of application Ser. No. 08/132,180, filed Oct. 6, 1993, now abandoned.

BACKGROUND OF THE INVENTION

The chemical name of the active substance mesna is sodium-2-mercaptoethane sulfonate. (Formula I)

$$HS-CH_2-CH_2-SO_3Na \qquad \text{Formula I}$$

Mesna for example protects the urinary tract from urotoxic symptoms in the treatment of tumor diseases with ifosfamide. In addition, mesna has been used for a long time as a mucolytic agent.

Mesna is a white hygroscopic powder with a characteristic odor. The substance is highly sensitive to oxidation and rapidly decomposes on contact with oxygen to form dimesna, (Formula II) particularly in a humid atmospheres.

$$NaSO_3-CH_2-CH_2-S-S-CH_2-CH_2-SO_3Na \qquad \text{Formula II}$$

Mesna has hitherto been administered orally, parenterally and by means of inhalation. All the dosage forms used are liquid formulations that are supplied in the form of ampoules or drinkable ampoules. Since mesna is very sensitive to oxidation and reacts in the presence of oxygen to form dimesna, which is poorly absorbed, the aqueous solution has to be protected against oxygen. For this purpose the solution is sealed into glass ampoules.

The solution for parenteral application is offered in 2 ml, 4 ml and 10 ml ampoules containing 10% mesna.

Mesna is generally given simultaneously with ifosfamide as well as 4 and 8 hours following administration of ifosfamide, in each case in a dose that corresponds to 20% of the ifosfamide dose, applied intravenously. The ifosfamide dose can be between 1 g/m² to 8 g/m² body surface. The corresponding mesna doses consequently are within a very broad range. There has been, therefore, a desire for multi-dose containers from which any quantity of injectable solution could be withdrawn with no waste, such as has occurred with opened ampoules. Such injection containers have also been intended to contain a larger volume of solution.

DAB (Deutseches Arzneibuch) 9 requires that multi-dose containers be preserved to provide protection against microbial contamination. The injectable solution in ampoules is very stable. This formulation has therefore been used and only one preservative, namely benzyl alcohol, which has been used throughout the world for parenterally applied aqueous systems, was added thereto. The pH value of this solution is adjusted to 6.5–8.5 with sodium hydroxide solution. The solution also contains a complexing agent since mesna forms colored complexes with heavy metal ions.

Stability storage tests showed, however, that these solutions were partially unstable. The degradation product was identified as mesna acetal with benzaldehyde

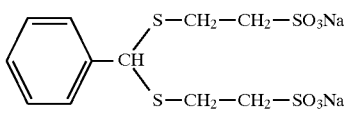

Benzaldehyde is present in the formulation because of oxidation of the benzyl alcohol used as preservative.

SUMMARY OF THE INVENTION

It has now been found surprisingly that this degradation product is only formed at pH values <7.5 and is not formed at an pH value of 7.5–8.5.

The invention thus relates to an injectable solution which contains, for each part of mesna:

(a) for example 0.00002–2.0 parts by weight
preferably 0.0001–1.0 parts by weight
in particular 0.0002–0.7 parts by weight of NaEDTA (sodium ethylene diamine tetraacetate-Sodium edetate) as complexing agent and (b) for example 0.0002–2.0 parts by weight
preferably 0.0003–1.7 parts by weight
in particular 0.0004–1.4 parts by weight
of sodium hydroxide for pH adjustment and (c) for example 0.001–30.0 parts by weight
preferably 0.01–20.0 parts by weight
in particular 0.018–12.0 parts by weight
of benzyl alcohol as preservative.

The amount by weight of mesna in an injectable solution of this type is generally in the range 1 mg per ml to 540 mg/ml. The solutions can be administered directly i.v. or designed as infusion solutions or concentrates as supplements to infusions.

The appropriate volumes are between 0.5 ml and 100 ml. Water for injection purposes is used as solvent.

In addition to the above listed auxiliary substances it is also possible to use:

complexing agents: for example the calcium disodium salt of edetic acid, citric acid, tartaric acid or salts of orthophosphoric acid.

The following are for examples of substances suitable for adjusting the pH:

sodium hydroxide, potassium hydroxide, tromethamine, sodium acetate, trisodium citrate, sodium monohydrogen phosphate, potassium monohydrogen phosphate.

Suitable preservatives are for example:

p-hydroxybenzoic acid ester, m-cresol, organomercuric compounds, chlorobutanol, quaternary ammonium compounds.

The preservatives may also be used in combination with benzyl alcohol.

To prepare the solution, 80–90%, preferably 85%, of the requisite amount of water (lacking in oxygen) are prepared and sodium edetate, benzyl alcohol and mesna dissolved with stirring and constant nitrogen gassing. When dissolution is complete the pH is adjusted to 8.0 by adding 10N sodium hydroxide solution. This solution is made up to the final volume with water (lacking in oxygen).

The solution obtained in this manner is sterilized by filtration through conventional pathogen-proof filters and then dispensed into appropriate containers for injectable preparations. The solution is covered with nitrogen during and after filtration. The storage time until filling into the injection containers, including the time to prepare the solution, should not exceed 4–5 hours.

For sterilization purposes, conventional pathogen-proof filters, for example conventional bacteria filters with a pore size of 0.2 μm are used. The glass vessels used are previously sterilized in conventional manner. The injection water used must be sterile and pyrogen-free and meet the requirements of the Deutsches Arzneibuch 10th 1991 edition. The injection vessels used are appropriately those made of tubular glass or blow-molded glass of hydrolytic class II (for example 10R, 30R, 50H), see in this connection Deutsches Arzneibuch 10, 1991 edition, VI.2.1. and DIN standards 58366 part 1 and part 5).

In addition, the injection vessels, as well as additional auxiliary substances, such as rubber stoppers and crimped caps, should meet the requirements of DIN standards 58366, part 2 and part 3, as well as 58367, part 1.

The volume of solution in the appropriate containers amounts, per container, to between 4 ml and 100 ml, preferably between 10 ml and 75 ml, in particular between 40 ml and 60 ml. The amount of mesna per glass vessel is, for example, 4 mg to 50 g, preferably 1 g to 7.5 g, in particular 4 g–6 g.

After dispensing the solution under aseptic conditions, the bottles are gassed with nitrogen to expel the oxygen and closed with injection stoppers. The filled injection bottles are sterilized in a steam sterilizer.

DETAILED DESCRIPTION OF PREFERRED EMBODIMENTS

The following examples illustrate the invention:

EXAMPLE 1

Injection bottle containing 50 ml of a 10% injectable mesna solution

| Composition | |
|---|---|
| mesna (INN) | 5000.0 mg |
| benzyl alcohol | 520.0 mg |
| sodium edetate | 12.5 mg |
| sodium hydroxide | 10.0–70.0 mg[1) 2)] |

Water for injection purposes 50.0 ml approx.=52.5 g

1) Used to adjust the pH value and is therefore variable
2) Used as 10N sodium hydroxide solution $25-175 \times 10^{-3}$ ml
3) The use of more or less is balanced by water for injection purposes The density of the solution is 1.05 g/ml.

Preparation of the Solution

85% of the amount of water for injection purposes (lacking in oxygen) are dispensed into a suitable vessel and the appropriate amounts of sodium edetate, benzyl alcohol and mesna dissolved therein with stirring and constant nitrogen gassing. The solution is adjusted to a pH value of 8.0 by addition of 10N sodium hydroxide solution and the resulting product is made up to the final volume with water for injection purposes (lacking in oxygen).

The water for injection purposes may contain a maximum of 1.5 ppm oxygen at 20° C. pH value, density and refractive index ($n^{20}$ 1.34–1.36) are determined as in-process controls. The solution is sterilized by filtration using a 0.2 μm membrane filter. The solution is covered with nitrogen during and after filtration. A Sartorius SM 11107 or SM 11307 or Pall Filter NRP is, for example, used as a conventional pathogen-proof filter. Particulate and bacterial contamination is avoided during storage of the solution before filling. Storage at room temperature (20°–22° C.) should not exceed 4–5 hours. Additional conventional prefilters may also be used for purposes of sterile filtration (for example Sartorius SM 13400 or Pall LPA) to protect the sterile filter.

Cleaning the Injection Bottles

DIN 50H/II, colorless 50 ml injection bottles are used as containers. They are flushed with hot and cold demineralized water and with air. All cleaning media are filtered to free them of suspended matter. To prevent recontamination due to particles from the air, the bottles are dried and sterilized using hot air (discontinuously at 180° C., 2 hours, continuous at 350° C. for 10 minutes).

The rubber stoppers (for example Helvoet FM 157/1 grey) used to close the injection bottles are cleaned using demineralized water and, for example, a cleaning agent consisting of non-ionic surfactants and phosphoric acid esters in aqueous solution (for example MB 70, Huber, Freiburg). The cleaned stoppers are rinsed free of fibers and fluff using water for injection purposes or filtered demineralized water. The stoppers cleaned in this manner are then sterilized using steam.

The injection bottles cleaned and sterilized in this manner are then gassed aseptically with nitrogen to displace the oxygen in the air, filled with 52 ml mesna solution and gassed again. Finally, the stoppers are positioned and secured with crimped caps. The filling volume is statistically monitored by then weighing the contents. The nominal filling amount is 52 ml=54.6 g. The residual oxygen content in the headspace of the injection bottle is also monitored.

The filled injection bottles are sterilized in a steam sterilizer (at least 120°/20 minutes).

The injection bottles are checked for incorrect closure, outer faults, clarity and particulate impurities.

EXAMPLE 2

Injection bottle with 50 ml of a 50% concentrate (w/V) for addition to infusion solutions:

| Composition: | |
|---|---|
| mesna | 25,000 g |
| benzyl alcohol | 0.520 g |
| Na EDTA | 0.0125 g |
| sodium hydroxide | 0.05–0.35 g | water for injection purposes ad 50,000 ml=61.0 g

The density of the concentrate is 1.22 g/ml 20° C. The preparation and sterile filtration of the solution, cleaning and sterilization of the bottles and rubber stoppers, filling, closing of the bottles and final sterilization are carried out as in Example 1.

What is claimed is:

1. A rubber-stopped sterile injection container containing a medication for preventing at least some of the side effects of azaphosdhorin comprising an injectionable mesna solution having a pH value between about 7.5 and about 8.5.

2. The rubber-stopped sterile injection container of claim 1, wherein the mesna solution consists essentially of mesna, a complexing agent, a pH adjuster, and a preservative.

* * * * *